(12) United States Patent
Giulianotti et al.

(10) Patent No.: US 10,368,949 B2
(45) Date of Patent: Aug. 6, 2019

(54) ROBOTIC SURGICAL STATION

(71) Applicant: THE BOARD OF TRUSTEES OF THE UNIVERSITY OF ILLINOIS, Urbana, IL (US)

(72) Inventors: Pier Giulianotti, Urbana, IL (US); Arturo Vittori, Urbana, IL (US); Andreas Vogler, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 904 days.

(21) Appl. No.: 14/897,639

(22) PCT Filed: Jun. 13, 2014

(86) PCT No.: PCT/US2014/042286
§ 371 (c)(1),
(2) Date: Dec. 10, 2015

(87) PCT Pub. No.: WO2014/201340
PCT Pub. Date: Dec. 18, 2014

(65) Prior Publication Data
US 2016/0135905 A1 May 19, 2016

Related U.S. Application Data

(60) Provisional application No. 61/834,504, filed on Jun. 13, 2013.

(51) Int. Cl.
*A61B 34/30* (2016.01)
*A61F 5/37* (2006.01)
(Continued)

(52) U.S. Cl.
CPC ............... *A61B 34/30* (2016.02); *A61F 5/37* (2013.01); *A61B 2018/00291* (2013.01);
(Continued)

(58) Field of Classification Search
CPC ............... A61B 19/22; A61B 19/2203; A61B 2019/223; A61B 2019/2207;
(Continued)

(56) References Cited

U.S. PATENT DOCUMENTS 2,742,900 A 4/1956 Giorgio et al.
3,239,843 A 3/1966 Lobelle
(Continued)

FOREIGN PATENT DOCUMENTS

CN 203168090 9/2013
GB 828731 A 2/1960
(Continued)

OTHER PUBLICATIONS

Corrected International Preliminary Report on Patentability for International Application No. PCT/US2014/042279 filed Jun. 13, 2014 on behalf of the Board of Trustees of the University of Illinois. dated Jan. 29, 2016.
(Continued)

*Primary Examiner* — David H Bollinger
(74) *Attorney, Agent, or Firm* — Steinfl + Bruno LLP

(57) ABSTRACT

A robotic surgical station is described. The robotic surgical station has a base configured to be fixed to the ground, a ring-shaped structure to which a patient bed and a plurality of robot arms are restrained at respective first and second mounts and a remote control unit that may be used by a surgeon to carry out a surgical intervention on a patient.

13 Claims, 11 Drawing Sheets

(51) Int. Cl.
*A61B 18/00* (2006.01)
*A61G 13/06* (2006.01)
*A61G 13/08* (2006.01)

(52) U.S. Cl.
CPC ........ *A61B 2034/304* (2016.02); *A61G 13/06* (2013.01); *A61G 13/08* (2013.01)

(58) Field of Classification Search
CPC .... A61B 2019/2211; A61B 2019/2215; A61B 2019/2219; A61B 2019/2223; A61B 2019/2226; A61B 2019/2234; A61B 2019/2238; A61B 34/30; A61B 2034/304; A61B 2018/00291; A61G 13/06; A61G 13/08; A61F 5/37
USPC ........ 606/130; 901/14, 15; 604/19; 600/411, 600/11; 128/845, 847, 870, 897, 899; 5/607, 608
See application file for complete search history.

(56) References Cited

U.S. PATENT DOCUMENTS

| | | |
|---|---|---|
| 3,783,863 A | 1/1974 | Kliever |
| 5,322,245 A | 6/1994 | Bassick |
| 5,626,151 A | 5/1997 | Linden |
| 5,975,081 A | 11/1999 | Hood et al. |
| 6,047,203 A | 4/2000 | Sackner et al. |
| 6,073,284 A | 6/2000 | Borders |
| 6,112,333 A | 9/2000 | Mazzei |
| 6,155,260 A | 12/2000 | Lavin et al. |
| 6,245,028 B1 | 6/2001 | Furst et al. |
| 6,401,278 B1 | 6/2002 | Hayes et al. |
| 6,460,187 B1 | 10/2002 | Siegel |
| 6,493,890 B2 | 12/2002 | Smeed |
| 6,792,623 B2 | 9/2004 | Luppi |
| 7,296,570 B2 | 11/2007 | Hutchinson |
| 8,033,281 B2 | 10/2011 | Kneale et al. |
| 2002/0138905 A1 | 10/2002 | Bartlett et al. |
| 2003/0097060 A1 | 5/2003 | Yanof et al. |
| 2004/0040064 A1 | 3/2004 | Mah et al. |
| 2004/0267145 A1 | 12/2004 | David et al. |
| 2006/0150335 A1 | 7/2006 | Dankbaar et al. |
| 2009/0235928 A1 | 9/2009 | Borsari |
| 2010/0031443 A1 | 2/2010 | Georgiev et al. |
| 2010/0242150 A1 | 9/2010 | Trouillot |
| 2011/0076771 A1 | 3/2011 | Gabriele et al. |
| 2011/0289644 A1 | 12/2011 | Beshlian |
| 2012/0136231 A1 | 5/2012 | Markel |
| 2012/0146784 A1 | 6/2012 | Hines et al. |
| 2012/0158074 A1 | 6/2012 | Hall |
| 2012/0246795 A1 | 10/2012 | Scheffler et al. |
| 2013/0085510 A1 | 4/2013 | Stefanchik et al. |
| 2013/0178870 A1 | 7/2013 | Schena |

FOREIGN PATENT DOCUMENTS

| | | |
|---|---|---|
| JP | 2006280534 | 10/2006 |
| JP | 2007175266 | 7/2007 |
| KR | 10-2011-0030038 A | 3/2011 |
| WO | 1992/18084 A1 | 10/1992 |
| WO | 1999/029235 A | 6/1999 |
| WO | 00/00152 | 1/2000 |
| WO | 03/097145 | 11/2003 |
| WO | 2005/102084 A1 | 11/2005 |
| WO | 2007/128571 | 11/2007 |

OTHER PUBLICATIONS

International Search Report for PCT/US2014/042279 filed Jun. 13, 2014 on behalf of The Board of Trustees of the University of Illinois, dated Nov. 4, 2014.
Written Opinion for PCT/US2014/042279 filed Jun. 13, 2014 on behalf of The Board of Trustees of the University of Illinois, dated Nov. 4, 2014.
International Search Report for PCT/US2014/042286 filed Jun. 13, 2014 on behalf of The Board of Trustees of the University of Illinois, dated Nov. 4, 2014.
Written Opinion for PCT/US2014/042286 filed Jun. 13, 2014 on behalf of The Board of Trustees of the University of Illinois, dated Nov. 4, 2014.
International Preliminary Report on Patentability for PCT/US2014/042286 filed Jun. 13, 2014 on behalf of The Board of Trustees of the University of Illinois, dated Nov. 30, 2015.
International Search Report and Written Opinion for PCT/US2014/042277 filed Jun. 13, 2014 on behalf of The Board of Trustees of the University of Illinois, dated Nov. 7, 2014.
International Search Report and Written Opinion for PCT/US2014/042281 filed Jun. 13, 2014 on behalf of The Board of Trustees of the University of Illinois, dated Oct. 20, 2014.
International Preliminary Report on Patentability for PCT/US2014/042281 filed Jun. 13, 2014 on behalf of The Board of Trustees of the University of Illinois, dated Jun. 26, 2015.
International Preliminary Report on Patentability for PCT/2014/042279 filed Jun. 13, 2014 on behalf of The Board of Trustees of the University of Illinois, dated Dec. 4, 2015.
International Preliminary Report on Patentability for PCT/2014/042277 filed Jun. 13, 2014 on behalf of The Board of Trustees of the University of Illinois, dated Dec. 15, 2015.

ROBOTIC SURGICAL STATION

CROSS REFERENCE TO RELATED APPLICATIONS

The present application is the US national stage of International Patent Application PCT/US2014/042286 filed internationally on Jun. 13, 2014, which claims priority to U.S. Provisional Application No. 61/834,504 filed on Jun. 13, 2013, which is hereby incorporated herein by reference in its entirety.

FIELD

The present disclosure generally relates to surgery robots and in particular to a robotic surgical station.

BACKGROUND

Operating rooms are currently mainly organized based on a 19th century pre-robotic environment. With the introduction of laparoscopic surgery and the following combination with robotics, a new era of surgery and operating room structure is emerging.

There are known surgery robots such as, for example, the "da Vinci" robotic surgery system developed by Intuitive Surgical, Inc. The "da Vinci" robotic surgery system comprises a surgery robot provided with a number of robotic arms or end effectors to which surgery instruments are connected. The robot is placed aside an operating table and remotely controlled by a surgeon by way of a control station comprising special handles and pedals allowing the surgeon to selectively drive the robotic arms and surgical instruments.

Other robotic surgery systems are known in the art. For example, U.S. 2013/0178870 discloses a robotic surgery system for supporting a patient and a robotic surgical manipulator. The robotic surgery system includes a base, a pillar coupled to the base at a first end and extending vertically upwardly to an opposing second end, and an attachment structure coupled to the second end of the pillar. A patient table is coupled to the attachment structure. A robot support arm has a first end coupled to the attachment structure. The robot support arm extends vertically upwardly from the first end to a second end. The robot support arm may further extends horizontally over the patient table to support a robotic surgical manipulator that will extend generally downward from the robot support arm toward a patient supported by the patient table to place an end effector of the robotic surgical manipulator adjacent a desired surgical site on the patient.

The patient table may be inclined relative to the ground in order to achieve by gravity positions of the internal organs of a patient that may be desirable for certain surgery procedures.

U.S. 2013/085510 discloses a similar robotic surgery system wherein robotic arms and a patient table are restrained to a pillar in turn mounted on a base. The patient table is operatively coupled to the robot and to an associated controller. The position of the patient can thus be controlled remotely using the robot, and the controller can have an awareness of the position and orientation of the patient with respect to the operating room and with respect to various components of the robot. Such systems can thus maintain a fixed frame of reference between the patient and one or more end effectors of the surgical robot, eliminating the need for recalibration of the system due to patient movement.

The availability of robotic surgery systems notwithstanding, a growing need to improve the quality of the operating room environment still exists, and more particularly a need to further improve and develop robotic surgery systems wherein robotic arms and a surgical table form a single integrated surgical station, which is an object according to an embodiment of the present disclosure.

SUMMARY

The present disclosure relates to a robotic surgical station comprising a base configured to be fixed to the ground, a ring-shaped structure to which a patient bed and a plurality of robot arms are restrained at respective first and second mounts and a remote control unit that may be used by a surgeon to carry out a surgical intervention on a patient. The ring-shaped structure is rotatable relative to the base about a roll axis parallel to the ground and passing through the center of the ring-shaped structure.

The robotic surgical station may also be rotatable relative to the base about a pitch axis parallel to the ground and perpendicular to said roll axis.

The first and second mounts of the ring-shaped structure may have a telescopic structure, thus allowing to adjust the mutual position of the patient's bed and the robotic arms.

According to an embodiment of the present disclosure, the robotic arms may be assembled on the ring-shaped structure at different locations so as to allow a surgeon to arrange them based on the requirements of a specific surgical intervention. To this aim the second mount of the ring-shaped structure comprises an annular frame having a hollow structure wherein electrical wires and cables are arranged and connected in parallel to a number of sockets configured to allow mechanical and electrical assembly of a respective number of robotic arms.

Differently from known robotic surgical systems that have a predetermined number of arms, the number of robotic arms that may be attached to the annular frame of the robotic surgical station according to an embodiment of the present disclosure may vary (i.e. "open platform") depending on the specific need of surgery. Hence, different and optimized setups of the surgical station may be achieved e.g. for prostate surgery, lung surgery and the like.

According to an embodiment of the present disclosure, the first and second mounts are rotatable about a yaw axis perpendicular to the ground and to the roll and pitch axes, so that the patient's bed and/or the arms may be rotated relative to the ring-shaped structure, for example, in order to ease preparation of a patient for surgery or the setup of the robotic arms and related surgical tools.

According to a further embodiment of the present disclosure, the patient's bed is configured to be removably mounted on the first mount. A patient can thus be arranged on the surgical bed and prepared for surgery before entering the operation room, wherein the surgical bed is connected to the surgical station. Moreover, the removal of the patient's bed allows to comfortably bring a patient back to his/her hospital room without transferring him/her to another bed.

Further advantages and features of the robotic surgical station according to the present disclosure will become clear to those skilled in the art from the following detailed and non-limiting description of embodiments thereof with reference to the attached drawings.

DETAILED DESCRIPTION

Figure 1:
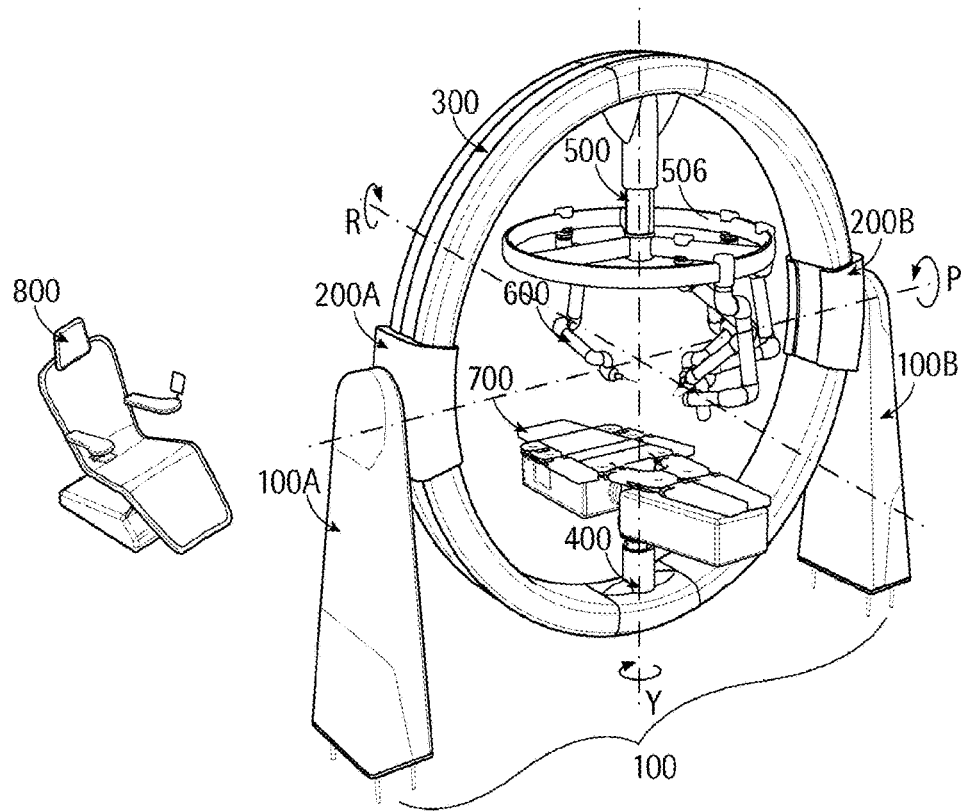
FIG. 1 is a perspective view of an embodiment of the robotic surgical station according to the present disclosure.
Figure 2:
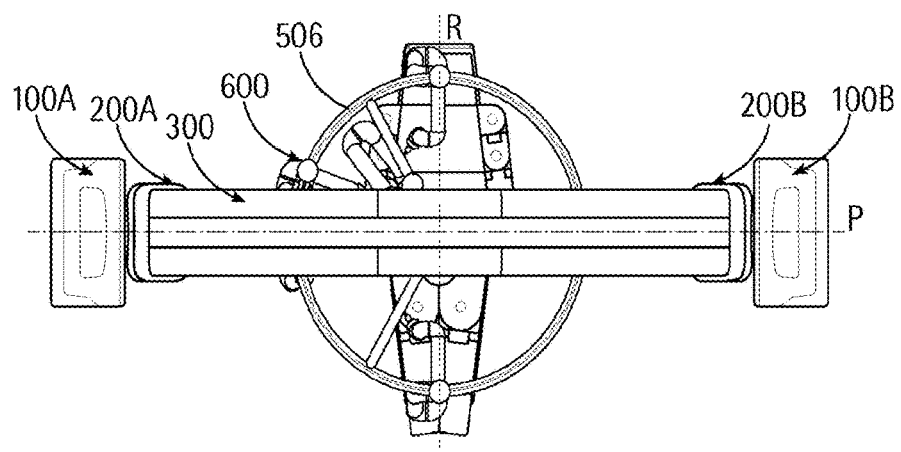
FIGS. 2 to 4 respectively show a top view, a front view and a side view of the robotic surgical station of FIG. 1.
Figure 3:
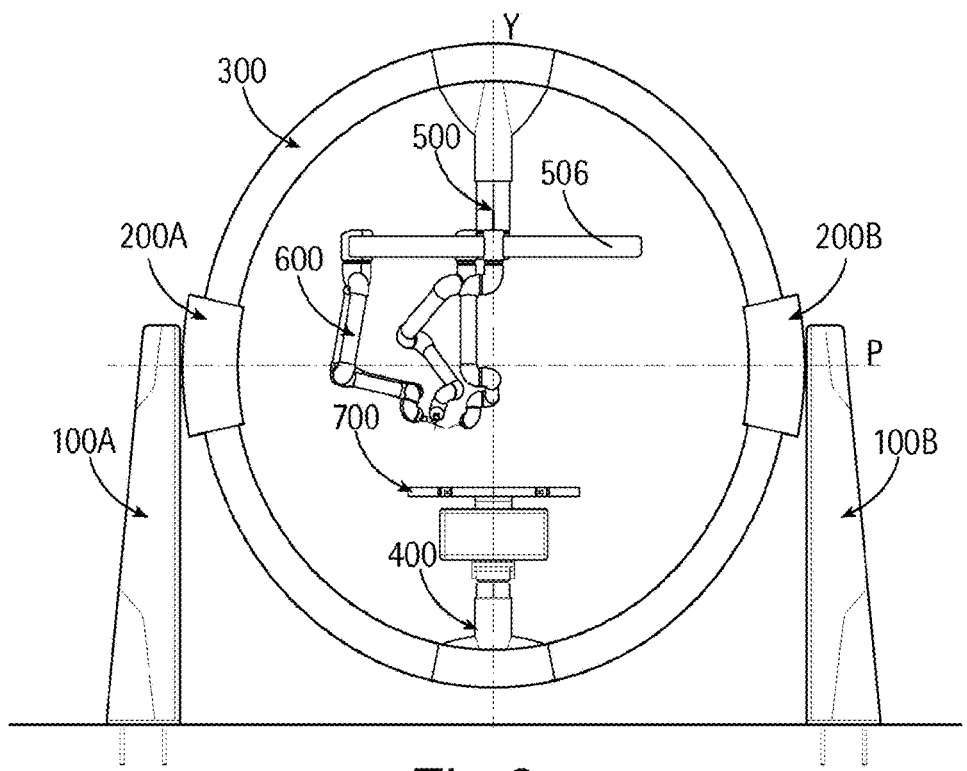
Figure 4:
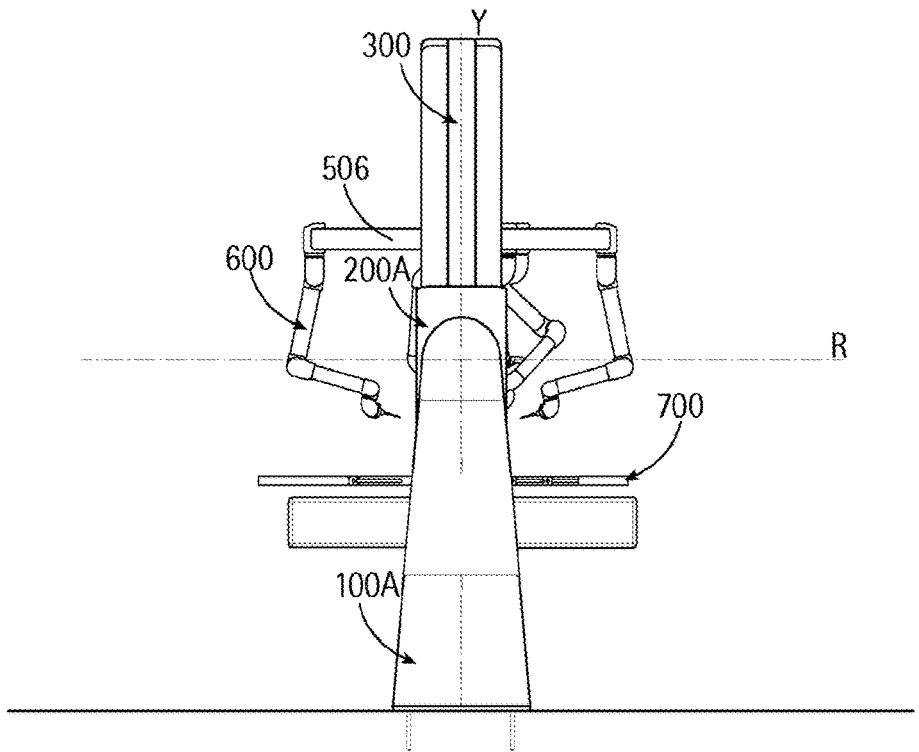

The robotic surgical station of the present disclosure comprises a base 100 configured to be fixed to the ground, a ring-shaped structure 300 to which a patient bed 700 and a plurality of robot arms 600 are restrained and operably connected. The robotic surgical station further comprises a remote control unit 800 that may be used by a surgeon to carry out a surgical intervention on a patient.

Referring to FIGS. 1 to 4, the base 100 of the robotic surgical station of an embodiment of the present disclosure comprises a pair of vertical uprights 100A and 100B extending perpendicularly to the ground. Each upright 100A, 100B comprises an arcuate member 200A, 200B protruding in a transverse direction therefrom. The uprights 100A and 100B are arranged such that the arcuate members 200A, 200B face each other. The arcuate members 200A, 200B are hollow bodies wherein the ring-shaped structure 300 is slidably fitted. The ring-shaped structure 300 is provided with a first mount 400 configured to support a patient bed 700 and with a second mount 500 supporting a frame 506 configured for the assembly of a plurality of robotic arms 600 that may be controlled by a surgeon from a remote control unit 800. The first and second mounts 400, 500 are arranged opposite to each other along a diameter of the ring-shaped structure 300.

In FIGS. 1 to 4, the first and second mounts 400, 500 are shown aligned in a vertical direction, i.e. with their axes substantially perpendicular to the ground. This is a default configuration of the robotic surgical station, wherein the patient bed 700 is substantially parallel to the ground.

Figure 5:
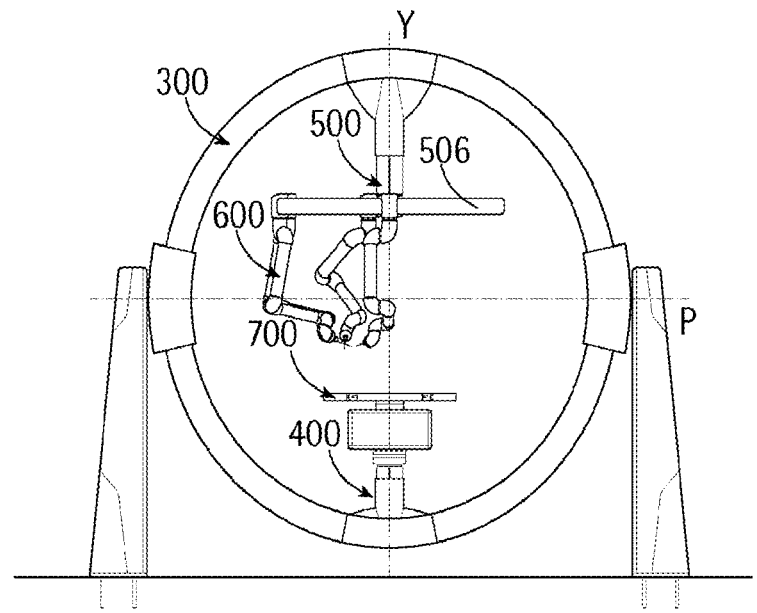
FIG. 5 shows a front view of the robotic surgical station wherein the ring-shaped structure is in a default position with the patient bed substantially parallel to the ground.
Figure 6:
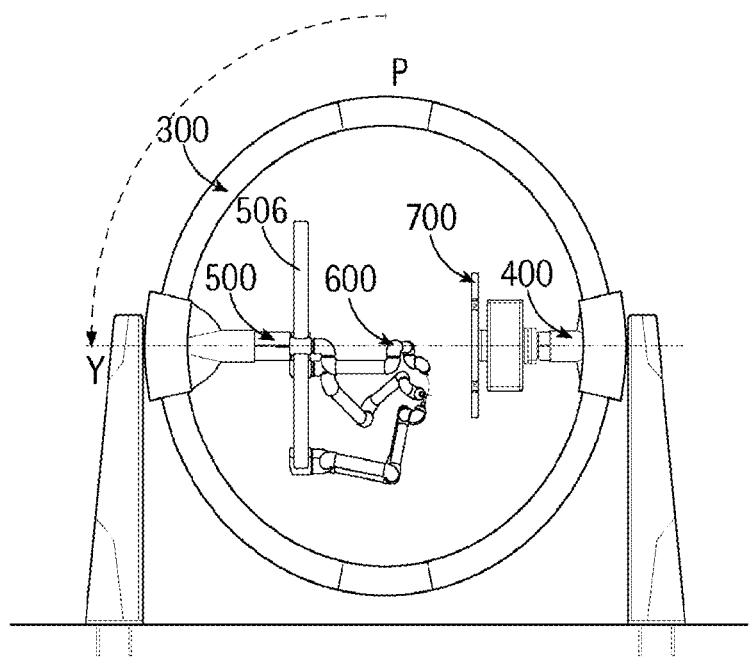
FIG. 6 shows a front view of the robotic surgical station wherein the ring-shaped structure is rotated by 90° counterclockwise.

According to an embodiment of the present disclosure, the ring-shaped structure 300 is rotatable relative to the base 100 about a roll axis R parallel to the ground and passing through the center of the ring-shaped structure 300. As shown in FIGS. 5 and 6 the ring-shaped structure 300 may e.g. be rotated by 90° clockwise or counterclockwise about the roll axis R so as to move the patient's bed 700 from a first position substantially parallel to the ground, corresponding to a traditional resting position of a surgical table, to a second position substantially perpendicular to the ground, which is often and often used in laparoscopic surgery to exploit gravity as a means to move the internal organs of a patient in order to create room for a better maneuvering of surgical instruments.

Due to the above-described configuration of the robotic surgical station, the rotation of the ring-shaped supporting structure 300 simultaneously determines a rotation of both the patient bed 700 assembled on the first mount 400 and of the robotic arms 600 restrained to the second mount 500. In other words, the robotic arms 600 may be moved in mechanical synchronization with the patient's bed 700, because they are mounted on the same ring-shaped supporting structure 300. Differently from known robotic surgical stations integrating a surgical table, wherein the robotic arms are configured to automatically follow the patient's bed when the latter is moved relative to the ground, in the robotic surgical station of an embodiment of the present disclosure the patient's bed and the robotic arms may be simultaneously moved thus maintaining their initial mutual positioning setup during the whole surgical intervention.

The advantage of this configuration over existing robotic surgical systems is that the synchronization between the bed and the robotic arms is inherently determined by the design of the whole surgical system. No need exists for wireless connections that may cause malfunctions of the components, i.e. bed and robotic arms, to be moved, as well as interruptions/disruptions of surgical procedures that might be dangerous for patients. According to an embodiment of the present disclosure, rotation of the ring-shaped structure 300 may be obtained by way of motorized rollers housed in the arcuate members 200A, 200B.

Figure 7:
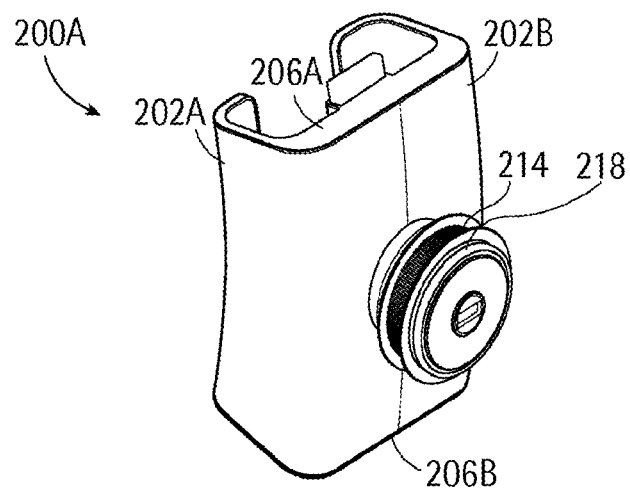
FIGS. 7 and 8 show an assembly and an exploded view of an arcuate member of one of the uprights supporting the ring-shaped structure, respectively.
Figure 8:
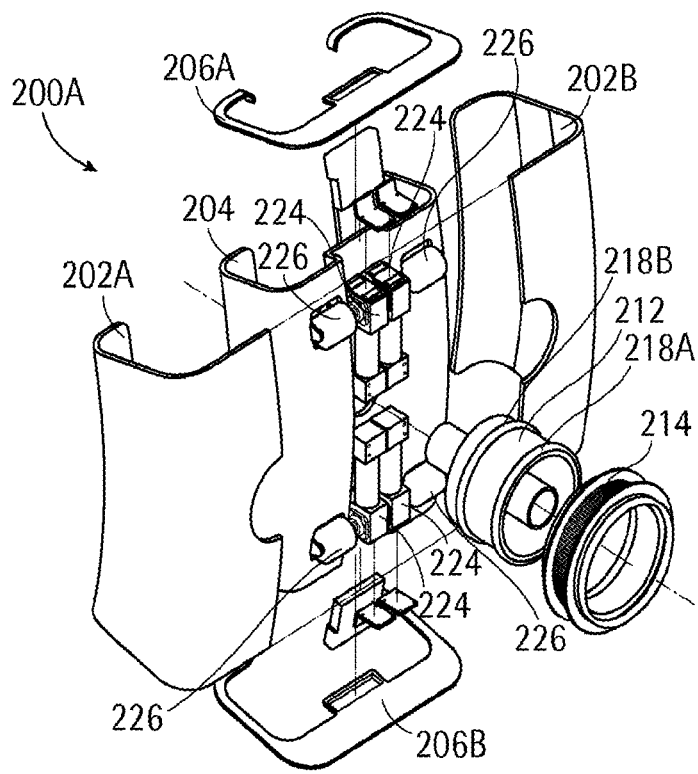

FIGS. 7 and 8 show an assembly and an exploded view of the arcuate member 200A, respectively. The rollers are indicated by reference numbers 226, while respective gear motors are indicated by reference number 224. In the illustrated embodiment four rollers 226 and four respective gear motors 224 are shown, but a different number of rollers and motors may be used as well.

Still with reference to FIGS. 7 and 8, according to an embodiment of the present disclosure the arcuate member 200A comprises an outer case having of a pair of half shells 202A, 202B. The outer case also comprises top and bottom covers 206A, 206B.

The arcuate member 200A further comprises an inner case 204 arranged inside the outer case. The rollers 226 and their motors 224 are assembled on the inner case 204. The outer case comprises a circular aperture formed in the half shells 202A, 202B wherein a pulley 214, a related rotor 212 and bearings 218A, 218B are fitted. These components allow to rotatably restrain the arcuate member 200A to its upright 100A as it will be described in the following. The arcuate member 200B comprises the same components of the arcuate member 200A.

According to a preferred embodiment of the present disclosure, the ring-shaped structure 300 is also rotatable about a pitch axis P that is parallel to the ground and perpendicular to the roll axis R. To this aim, the arcuate members 200A, 200B are rotatably restrained to the uprights 100A and 100B of the base 100 and operably connected to respective motors housed in the uprights 100A, 100B e.g. by way of toothed belts.

Figure 9:
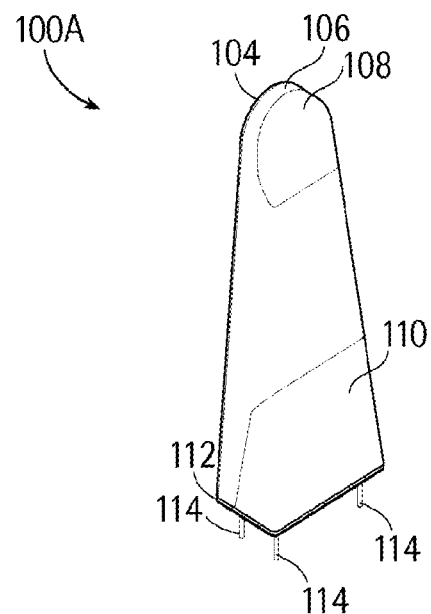
FIGS. 9 and 10 show an assembly and an exploded view of one of the uprights supporting the ring-shaped structure, respectively.
Figure 10:
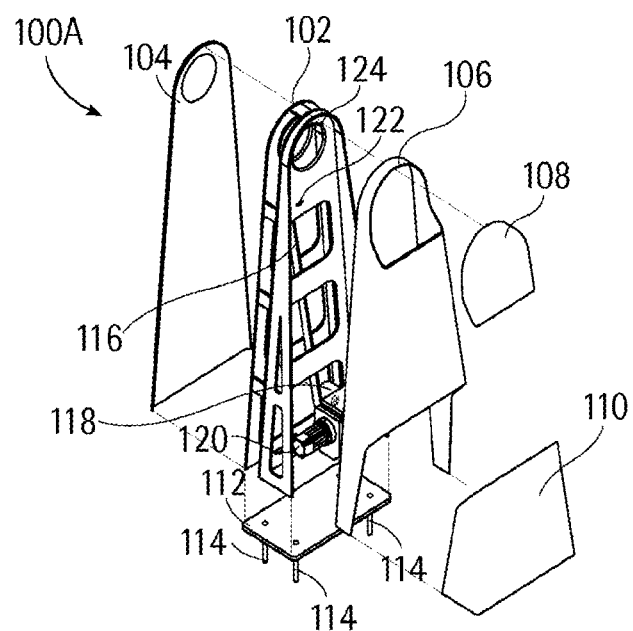

FIGS. 9 and 10 show an assembly and an exploded view of the upright 100A, respectively. The upright 100A comprises a structural support 102 and a protective casing e.g. made up of a front and a back shroud 104, 106. The casing also comprises a base member 112 is arranged at the bottom of the upright 100A and configured to allow to restrain it to the ground e.g. by way of screws 114. The casing may also comprise inspection shrouds 108 and 110 e.g. removably connected to the back shroud 106. A gear motor 120 is arranged at the basis of the structural support 102. The motor comprises a pulley 118 driving a toothed belt 116 configured to be connected to the pulley 214 of the arcuate member 200A shown in FIGS. 7 and 8. The structural support 102 comprises a mounting 124 formed in its top portion and suitable to receive the pulley 214 of the arcuate member 200A. The upright 100B comprises the same components of the upright 100A.

Figure 11:
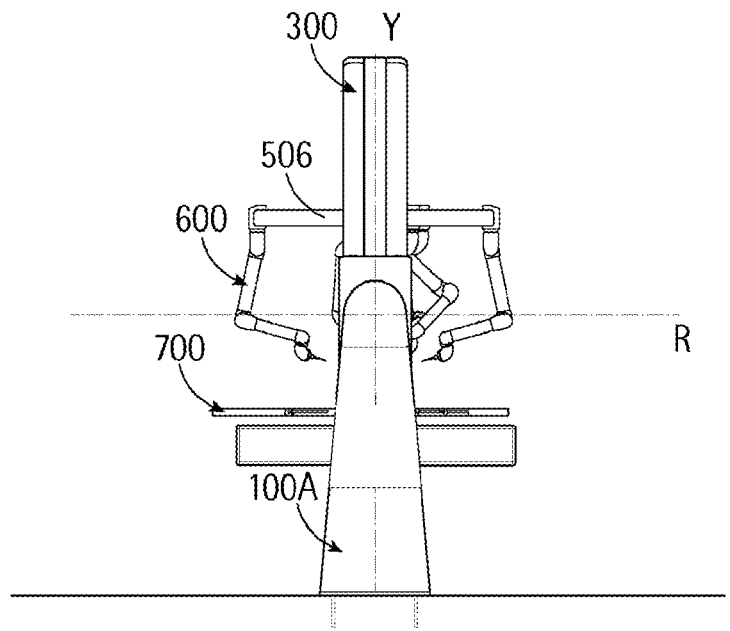
FIGS. 11 and 12 schematically show clockwise or counterclockwise rotations of the ring-shaped structure about a pitch axis.
Figure 12:
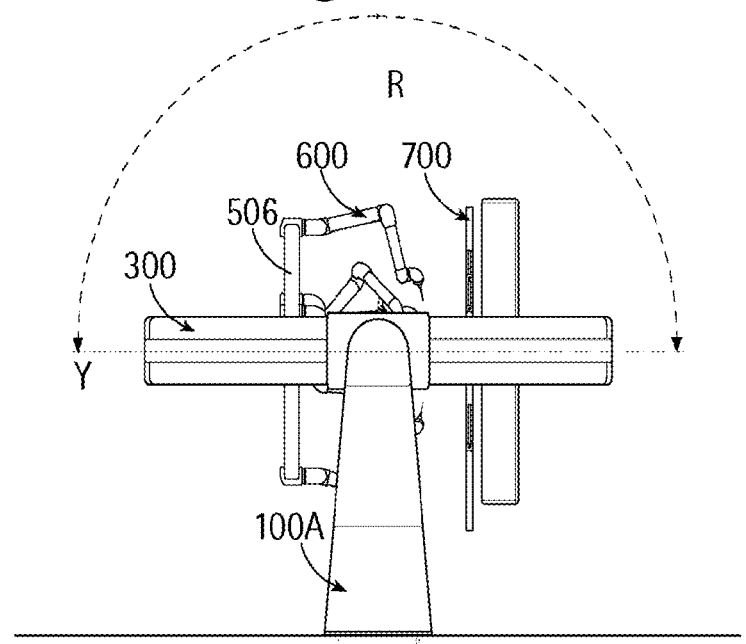

FIGS. 11 and 12 schematically show how the ring-shaped structure 300 may be rotated e.g. by 90° clockwise or counterclockwise about the pitch axis P.

Thanks to this configuration of the robotic surgical station according to an embodiment of the present disclosure, the patient's bed 700 and the robotic arms 600 may simultaneously be rotated about two horizontal axes, namely the roll axis R and the pitch axis P, while maintaining their initial mutual positioning setup. This allows a surgeon to move the patient relative to the ground according to two rotational degrees of freedom.

According to an embodiment of the present disclosure, the first and second mounts 400, 500 may advantageously have a telescopic structure so as to allow to adjust the relative distance between the patient's bed 700 and the robotic arms 600 in particular during the initial setup phase.

Figure 13:
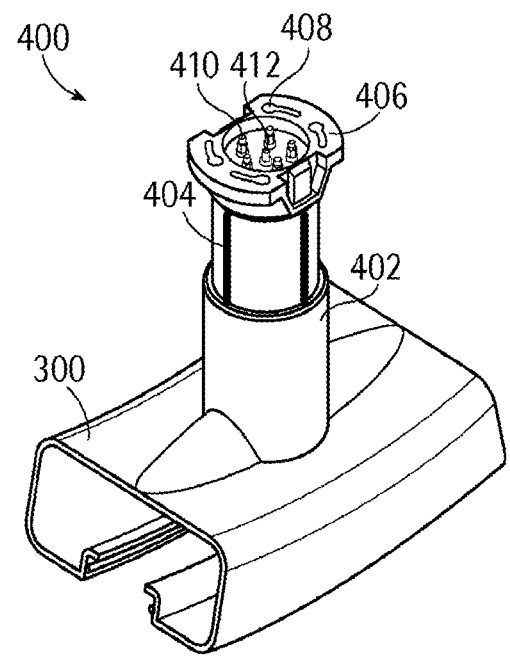
FIG. 13 is a detailed view showing a portion of the ring-shaped structure wherein the first mount is assembled.

FIG. 13 is a detailed view showing a portion of the ring-shaped structure 300 wherein the first mount 400 is assembled. For simplicity's sake the patient's bed is not shown in FIG. 13.

The first mount 400 has a telescopic structure comprising an outer cylinder 402 and an inner cylinder 404 slidably fitted in the outer cylinder 402. The free end of the inner cylinder 404 comprises a flange 406 on which the patient's bed 700 is assembled.

The above described first mount 400 may be configured as a hydraulic linear actuator or as an electromechanical linear actuator, the latter e.g. comprising a gear motor engaging a thread profile formed inside the outer cylinder 402.

Figure 14:
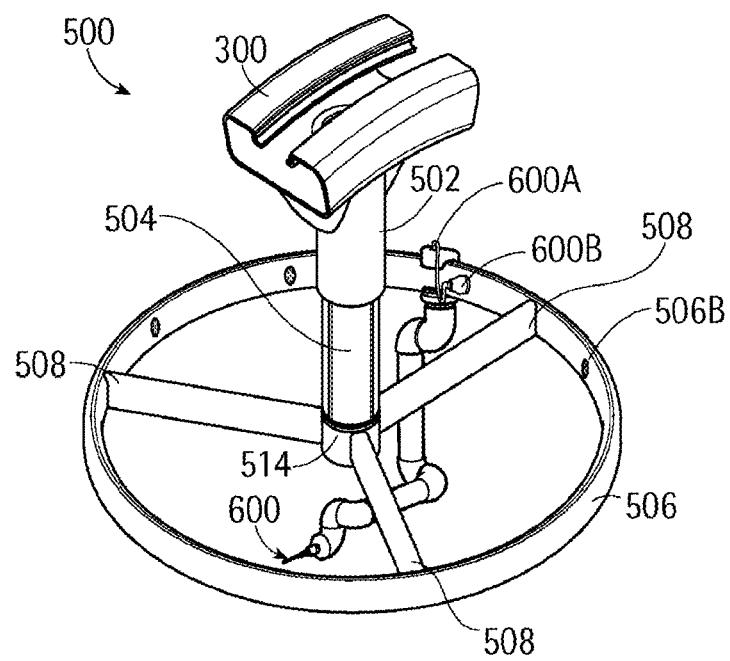
FIG. 14 is a detailed view showing a portion of the ring-shaped structure wherein the second mount is assembled.

FIG. 14 is a detailed view showing a portion of the ring-shaped structure 300 wherein the second mount 500 is assembled. For simplicity's sake only one robotic arm 600 is shown in FIG. 14.

The second mount 500 has a telescopic structure comprising an outer cylinder 502 and an inner cylinder 504 slidably fitted in the outer cylinder 502. The free end of the inner cylinder 504 comprises an annular frame 506 allowing to assemble the robotic arms 600. The annular frame 506 is restrained to the inner cylinder by way of radial members 508.

Similarly to the first telescopic mount 400 also the above described second telescopic mount 500 may be configured as a hydraulic linear actuator or as an electromechanical linear actuator, the latter e.g. comprising a gear motor engaging a thread profile formed inside the outer cylinder 502.

According to a preferred embodiment of the present disclosure, the annular frame 506 is configured to allow assembly of the robotic arms 600 at different operating positions. This configuration is advantageous, because it allows to assemble the robotic arms 600 based on a surgeons' needs in the frame of a specific surgical intervention. To this aim, the annular frame 506 is configured as a hollow structure wherein electrical wires and cables 506A are arranged along its inner periphery and are connected in parallel to a number of sockets 506B configured to allow electrical assembly of the robotic arms 600. As it may be seen, the arms 600 may be e.g. snap fitted on the annular frame 506 by way of respective clamps 600A and electrical plugs 600B of the arms 600 may be fitted in respective sockets 506B. Hence, mechanical and electrical connection of the arms 600 may be achieved in a simple, quick and effective manner.

Figure 15:
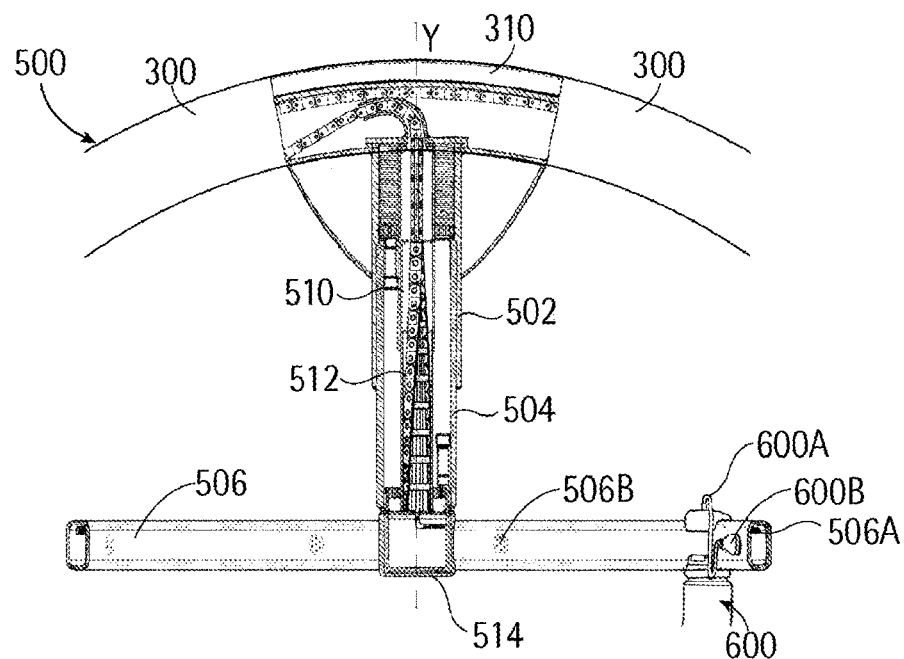
FIG. 15 is a cross-sectional view showing cable routing through the second mount and the ring-shaped structure fixed thereto.

As shown in FIG. 15, the electrical wires reach the annular frame through a first channel 310 formed in the ring-shaped structure 300 and through a second channel 510 formed coaxially to the second mount 500. The electrical wires and cables 506A may advantageously be guided by way of a cable chain 512 housed in the first and second channels 310, 510.

Figure 16:
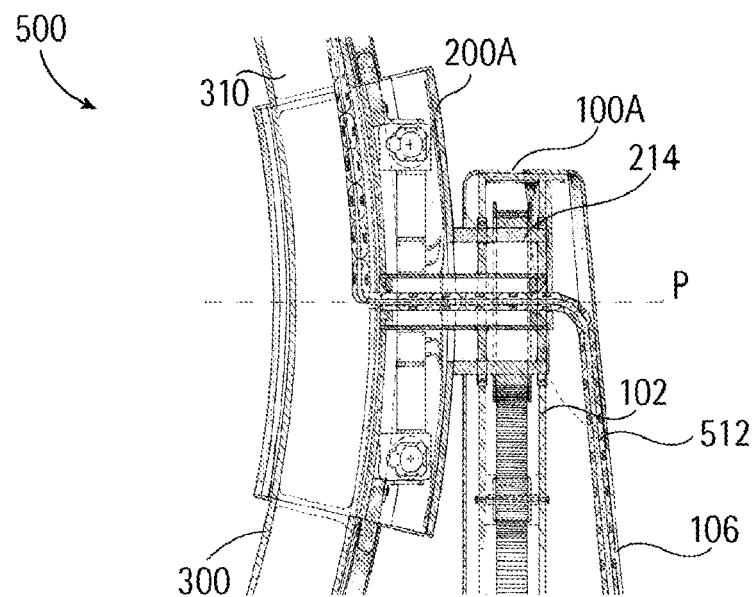
FIG. 16 is a cross-sectional view cable routing through one of the arcuate members and uprights of the ring-shaped structure.

As shown in FIG. 16, the cable chain 512 runs through the channel 310 of the ring-shaped structure 300 and exits therefrom through one of the arcuate members 200A, 200B, e.g. through the arcuate member 200A, e.g. coaxially to the pulley 214 and is further guided along the related upright 100A e.g. along the casing back shroud 106.

According to an embodiment of the present disclosure, both the first and second mounts 400, 500 are rotatable about a yaw axis Y perpendicular to the ground and to the roll and pitch axes. Thanks to this feature, the surgical station may have three rotational degrees of freedom, i.e. rotation about roll, pitch and jaw axis.

To this aim, a gear motor may e.g. be arranged inside the inner cylinder 404, 504 of each mount 400, 500 and a related rack may be formed at the inner periphery of the flange 406 and of the attachment member 514 of the annular frame 506.

This feature according to an embodiment of the present disclosure allows to rotate the patient's bed 700 and the robotic arms 600 relative to the ring-shaped structure 300 parallel to the ground depending on specific needs of the surgeon's staff. Hence optimal positioning of the patient's bed 700 and/or of the robotic arms 600 may be achieved.

Rotations of the patient's bed 700 and of the robotic arms 600 about the yaw axis Y may be simultaneous similarly to the other movements of the surgical station, thus allowing to maintain the mutual positioning set up. Rotations of the patient's bed 700 and the robotic arms 600 about the yaw axis Y may also be not simultaneous, e.g. in order to allow to prepare the patient for surgery or to move him/her from the surgical station to a hospital bed for transportation to a hospital room.

According to an embodiment of the present disclosure, the patient's bed may advantageously be configured to be removably mounted on the first mount 400.

To this aim the patient's bed 700 comprises a flange 702 arranged at the surface opposite to the surface 700A intended to receive a patient and provided with engaging means configured to removably fit corresponding engaging means provided on the flange 406 formed at the free end of the first mount 400.

Figure 17:
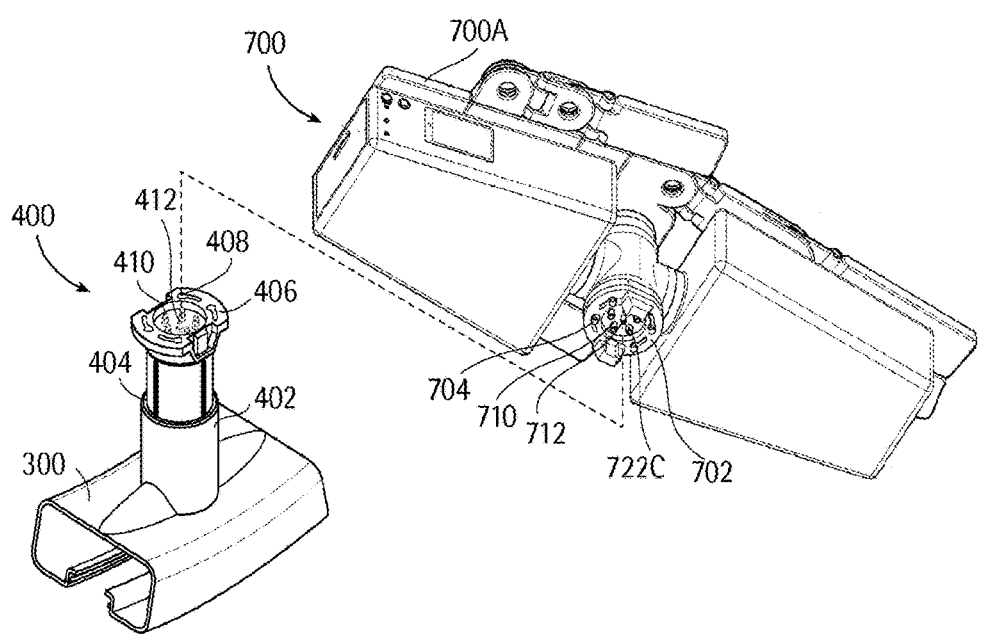
FIG. 17 is a perspective exploded view showing the patient's bed and the respective mount and their engaging means.

Now referring to FIG. 17, the engaging means may e.g. be mushroom-shaped posts 704 provided on the patient's bed flange 702 engaging respective slots 408 formed on the flange 406 of the first mount 400.

The patient's bed 700 may advantageously be provided with a life supporting unit configured to provide a patient with anesthetic gas, oxygen and the like. Gases may be supplied to the life supporting unit through respective supply ducts arranged coaxially to the first mount 400 and along the ring-shaped structure 300. The ducts may exit the ring-shaped structure 300 through one of the uprights 100A, 100B. Valves 410 allowing to connect the supply ducts to respective pipes intended to serve the patient may be provided at the flange 406 of the first mount 400, as shown in FIG. 17. Corresponding valve connectors 710 are provided in the flange 702 of the bed 700.

The patient's bed 700 may also be advantageously provided with instruments allowing to monitor the patient's vital signs. Electric wires and cables may be arranged coaxially to the first mount 400 and along the ring-shaped structure 300. The ducts may exit the ring-shaped structure 300 through one of the uprights 100A, 100B. Electrical connectors 412 may be arranged in the flange 406 aside the valves. Corresponding electrical connectors 712 are provided in the flange 702 of the bed 700.

According to a preferred embodiment of the present disclosure, the patient's bed is made up of individually movable portions allowing to arrange a patient in the most suitable position required by the surgical intervention that has to be carried out. As shown in FIG. 1, the bed 700 e.g. comprises individually movable arms and leg portions that can be pivoted relative to the bed frame about respective horizontal axes parallel to the bed frame and to vertical axes perpendicular thereto.

The bed 700 may advantageously be provided with integrated actuators allowing to selectively move these portions. Such actuators may e.g. be electromechanical or hydraulic actuators. The electrical wires and cables needed to drive these actuators may be arranged coaxially to the first mount 400 and along the ring-shaped structure 300. Wires and cables may exit the ring-shaped structure 300 through one of the uprights 100A, 100B.

According to a further embodiment of the present disclosure, the surgical station may be provided with a vacuum system associated with the patient's bed and allowing to restrain a patient thereon without resorting to traditional straps and fasteners.

Figure 18:
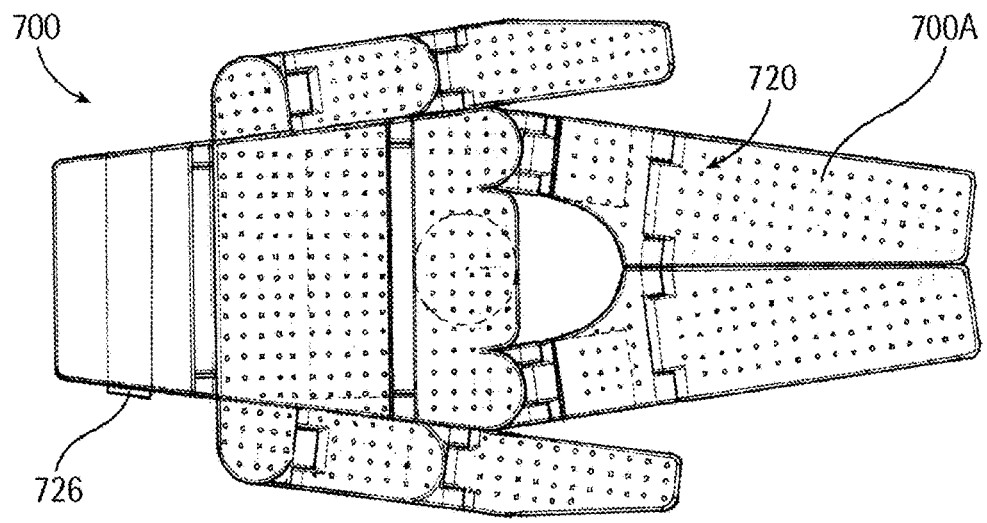
FIGS. 18 and 19 are a top view and a cross sectional view, respectively, schematically showing a vacuum system associated with the bed of the robotic surgical station.
Figure 19:
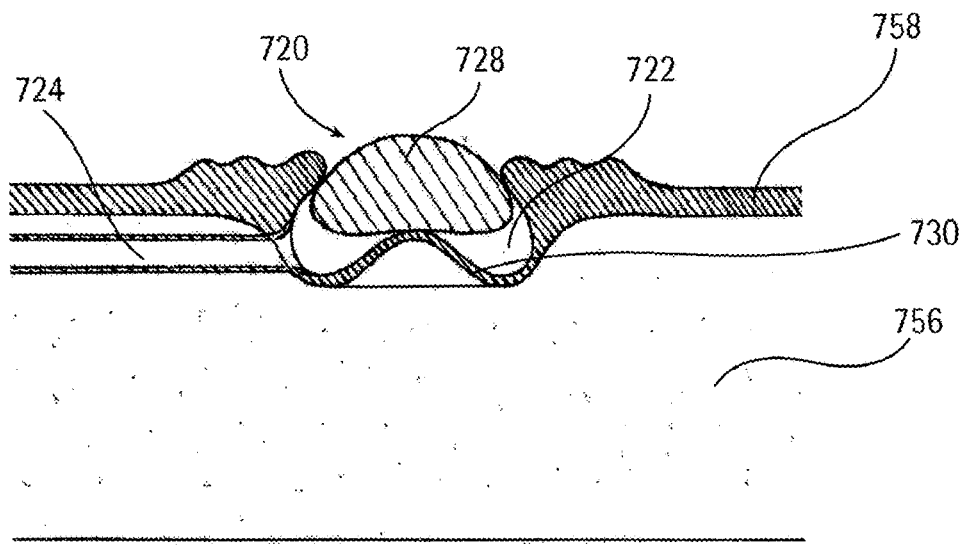

Referring to FIGS. 18 and 19, a number of apertures 720 are formed on the surface 700A of the bed 700 intended to receive a patient and respective cavities 722 are arranged under said apertures 720. The cavities 722 are respectively connected to a network of suction ducts 724 formed in the bed structure and allowing to suck air through the apertures 720.

The suction ducts 724 are connected to a common suction port 726 e.g. arranged along one side of the bed 700, which may in turn be connected to a remote suction unit provided in a operation room.

By operating the remote suction unit a patient laying flat on the surface 700A may thus be restrained thereon by sucking air without resorting to traditional straps and fasteners.

Since the patient does not cover the whole bed surface 700A and due to the fact that every patient has a different size, the vacuum system is advantageously configured so as to active only at the portions of the surface 700A that are actually covered by the patient. To this aim selectively operatable closing means are provided at each aperture 720. As schematically shown in the cross section of FIG. 19, a plug 728 is fitted within every one of the cavities 722 arranged under the respective apertures 720. The plugs 728 are housed in the respective cavities 722 and urged against the respective apertures 720 by way of elastic means 730 so as to close them. In the illustrated embodiment, such means are e.g. formed as a dome-shaped spring made of a resilient polymeric material. The spring may advantageously be integrally formed in the layer forming the bed surface 700A wherein the apertures 720, the cavities 722 and the suctions ducts 724 of the vacuum system are formed.

Thanks to the above described configuration, when no patient is on the surface 700A of the bed 700 all the apertures 720 are closed. When a patient is arranged on the surface 700A a number plugs 728 are depressed under the patient's weight, so that a respective number of apertures 720, related cavities 722 and suctions ducts 724 are opened and air may be sucked therethrough. Hence, an active portion of the vacuum system so configured is directly and precisely determined by the patient laying on the surface 700A.

In the illustrated embodiment the bed surface 700A has a multilayer structure and the suction system is formed in an upper layer 758 thereof. The bed surface 700A also comprises a backing layer 756 supporting the upper layer 758.

It is understood that the foregoing detailed description is merely illustrative and is not to be taken as a limitation of the scope of an embodiment of the present disclosure, which is defined solely by the appended claims and their equivalents. Various changes and modifications to the disclosed embodiments will be apparent to those skilled in the art.

The invention claimed is:

1. A robotic surgical station, comprising:
   i) a base configured to be fixed to the ground;
   ii) a ring-shaped structure to which a patient bed and a plurality of robot arms are restrained at respective first and second mounts; and
   iii) a remote control unit that may be used by a surgeon to carry out a surgical intervention on a patient,
      wherein the ring-shaped structure is rotatable relative to the base about a roll axis configured to be parallel to the ground and passing through the center of the ring-shaped structure.

2. The robotic surgical station of claim 1, wherein the base comprises a pair of vertical uprights configured to be extending perpendicularly to the ground, each upright comprising an arcuate member protruding in a transverse direction therefrom and wherein the uprights are arranged such that said arcuate members face each other, the arcuate members being hollow bodies wherein the ring-shaped structure is fitted.

3. The robotic surgical station of claim 2, further comprising motorized rollers housed in the arcuate members, said motorized rollers contacting the ring-shaped structure in order to allow rotation thereof.

4. The robotic surgical station of claim 1, wherein said first and second mounts of the ring-shaped structure are arranged opposite to each other along a diameter thereof.

5. The robotic surgical station of claim 1, wherein the ring-shaped structure is also rotatable relative to the base about a pitch axis configured to be parallel to the ground and perpendicular to said roll axis.

6. The robotic surgical station of claim 5, wherein the arcuate members are rotatably restrained to the uprights and operably connected to respective motors housed therein by way of toothed belts.

7. The robotic surgical station of claim 1, wherein the first and second mounts have a telescopic structure.

8. The robotic surgical station of claim 7, wherein the first and second mounts are hydraulic or electromechanical linear actuators.

9. The robotic surgical station of claim 1, wherein the frame associated with the second mount is a hollow structure wherein electrical wires and cables are arranged along its inner periphery and connected in parallel to a number of sockets configured to allow mechanical and electrical assembly of a respective number of robotic arms.

10. The robotic surgical station of claim 1, wherein both the first and second mounts are rotatable about a yaw axis configured to be perpendicular to the ground and to the roll and pitch axes.

11. The robotic surgical station of claim 1, wherein the patient's bed is configured to be removably mounted on the first mount and wherein the patient's bed comprises a flange provided with engaging means configured to fit corresponding engaging means provided on a flange formed at the free end of the first mount.

12. The robotic surgical station of claim 1, further comprising a vacuum system allowing to restrain a patient to the patient's bed, said vacuum system comprising apertures formed on the surface of the bed intended to receive a patient and respective cavities arranged under said apertures, said cavities being respectively connected to a network of suction ducts formed in the bed structure and allowing to suck air through the apertures.

13. The robotic surgical station of claim 12, wherein a plug is fitted within each one of the cavities arranged under the respective apertures and wherein the plugs are housed in the respective cavities and urged against the respective apertures by way of elastic means so as to close them.

* * * * *